United States Patent [19]

Schultz

[11] 4,344,438

[45] Aug. 17, 1982

[54] OPTICAL SENSOR OF PLASMA CONSTITUENTS

[75] Inventor: Jerome S. Schultz, Ann Arbor, Mich.

[73] Assignee: The United States of America as represented by the Department of Health, Education and Welfare, Washington, D.C.

[21] Appl. No.: 144,043

[22] Filed: Apr. 28, 1980

Related U.S. Application Data

[63] Continuation-in-part of Ser. No. 930,659, Aug. 2, 1978, abandoned.

[51] Int. Cl.$^3$ .................................................. A61B 5/00
[52] U.S. Cl. ...................................................... 128/634
[58] Field of Search .......................... 128/633, 634, 631; 356/39; 23/230 B, 901; 424/12; 250/364, 365

[56] References Cited

U.S. PATENT DOCUMENTS

| | | | |
|---|---|---|---|
| 3,123,066 | 3/1964 | Brumley | 128/2 |
| 3,638,639 | 2/1972 | Merrill | 128/2 |
| 3,785,772 | 1/1974 | Coggeshall | 23/253 R |
| 3,787,119 | 1/1974 | Rybak | 356/73 |
| 3,837,339 | 9/1974 | Aisenberg et al. | 128/631 |
| 3,939,350 | 2/1976 | Kronick et al. | 250/365 |
| 3,992,631 | 11/1976 | Harte | 250/365 |

OTHER PUBLICATIONS

Ransom, J. P., *Practical Competitive Binding Assay Methods*, C. V. Mosby Co., St. Louis., 1976, pp. 45–47.
Schultz, J. S. et al., *Biotech. & Bioengng. Symp.*, No. 9, 65–71, (1979).

*Primary Examiner*—Henry J. Recla
*Assistant Examiner*—Francis J. Jaworski
*Attorney, Agent, or Firm*—Browdy and Neimark

[57] ABSTRACT

A system for monitoring low molecular weight compounds in blood plasma in the body by optical means includes a chamber which can be inserted into the blood stream and which contains specific receptor sites for the plasma constituent to be analyzed. The chamber interior is isolated from the blood by a dialysis membrane which permits the plasma constituents to diffuse into the chamber. A competing ligand for the receptor sites is placed within the chamber, but due to its relatively large molecular size the competing ligand cannot escape through the dialysis membrane into the bloodstream. Light emitted or absorbed by the competing ligand gives a measure of the concentration of the selected low molecular weight compounds in the blood.

14 Claims, 10 Drawing Figures

OPTICAL SENSOR OF PLASMA CONSTITUENTS

The invention described herein was made in the course of work conducted under a grant or award from the Department of Health, Education and Welfare.

This is a CIP of parent, copending application Ser. No. 930,659, filed Aug. 2, 1978, now abandoned, the contents of which are hereby incorporated by reference.

FIELD OF THE INVENTION

The invention relates to devices for measuring the concentration of specific constituents in blood in the body, or in other complex fluid media.

BACKGROUND OF THE INVENTION

Many medical diagnoses depend upon measurement of the concentration of the constituents of plasma. One method of measuring these concentrations is to withdraw blood from the patient and then analyze the blood. The patent to Coggeshall, U.S. Pat. No. 3,785,772, for example, discloses a device having a pair of syringes to withdraw blood from a patient, a dialysis membrane to separate a particular blood constituent from the blood, a reactant which reacts with the chosen blood constituent to form a reactant-blood constituent complex, the concentration of which is proportional to the concentration of the blood constituent, and a detector to determine the concentration of the reactant-blood constituent complex. Coggeshall, however, must replace the reactant after each measurement because the reactant and the blood constituent form an irreversible complex, and the Coggeshall system cannot give measurement of the instantaneous change in the concentration of the blood constituent in the blood, because much time is taken to remove the blood from the body and obtain a reaction with the reactant.

Merrill, U.S. Pat. No. 3,638,639, also shows measurement of blood constituents outside the body. In the Merrill patent, a catheter is inserted into the blood and lipids are passed through a membrane in the catheter and are dissolved in a solvent which is sent out of the body to be analyzed.

The Kronick et al U.S. Pat. No. 3,939,350 shows a system for carrying out immunoassays using fluorescense to indicate the presence of a ligand to be detected. An analog liquid is bound to a transparent sheet and contacted with aqueous assay solution containing the ligand to be detected associated with fluorescent molecules. The ligands become bonded to the sheet and light is passed therethrough to cause fluorescense.

Brumley, U.S. Pat. No. 3,123,066, Polyanya, U.S. Pat. No. 3,461,856, and Rybak, U.S. Pat. No. 3,787,119, all disclose means to measure properties of the blood in vivo. They comprise optical catheters inserted into the blood for measuring the intensity of light reflected from the blood, thereby indicating the blood's oxygen content. In addition, Rybak can measure blood flow and blood pressure. None of the above-mentioned patents are specifically designed, however, for measuring the concentration of low molecular weight plasma constituents, such as glucose.

Some probes have been devised to measure low molecular plasma constituents, but these are based upon electrochemical reaction. The response of these devices is related to the diffusion rate across the membrane of the probe. Since the membranes used to separate the active electrode from the plasma become fouled after a period of time, the calibration characteristics of the device change with time, making the device inaccurate.

SUMMARY OF THE INVENTION*

It is an object of the invention to overcome the deficiencies of the prior art.

*See Schultz et al, "Affinity Sensors for Individual Metabolites", *Biotechnology and Bioengineering*, March 1980, hereby incorporated by reference.

It is further an object of the invention to provide for improved measurement of the concentration of low molecular weight plasma constituents in vivo.

It is another object of the invention to provide device to measure the concentration of low molecular weight plasma constituents in vivo.

It is a still further object of the invention to provide a device to measure the concentration of low molecular weight plasma constituents in vivo by optical means.

It is still another object of the present invention to provide a device to optically measure the concentration of low molecular weight plasma constituents in vivo using a specific receptor site which can reversibly combine with the low molecular weight plasma constituent and a competing ligand.

The device which achieves these objectives comprises a chamber, inserted into the bloodstream, having a dialysis membrane which allows selected plasma constituents to pass therethrough and enter the chamber. The chamber contains specific receptor sites, e.g. in the form of binding agents, each of which reversibly binds with one of the selected plasma constituents; the chamber also contains competing ligands, which compete with the plasma constituents for the specific receptor sites, e.g. on the binding agents. The competing ligands are chosen for their particular optical properties and molecular size so that they do not escape from the chamber through the membrane into the bloodstream. The intensity of light emitted from or absorbed by the receptor-site/competing-ligand complexes or the competing ligand alone is measured, and gives a quantitative indication of the concentration of plasma constituents in the blood.

BRIEF DESCRIPTION OF THE DRAWINGS

FIG. 5a is a schematic side view of a third embodiment, and FIG. 5b is a detailed schematic side view of the chamber of the embodiment of FIG. 5a.

DETAILED DESCRIPTION OF EMBODIMENTS

The concept of the invention is to confine a specific receptor site or exchanger within a defined spatial region along with another compound called a competing-ligand, which can reversibly bind to the specific receptor sites. A competing-ligand is selected which competes for the same receptor sites with the substance in the blood plasma to be measured or assayed, called the assay-ligand. While the receptor sites and the competing-ligand are confined within a spatial region called the analysis chamber by suitable barriers or membranes, such barriers or membranes are arranged so that the assay-ligand can fully diffuse between the device chamber and the test fluid, e.g. blood in the case of the illustrated embodiments.

The receptor site and the competing-ligand combination are chosen so that one of the substances, i.e. either the competing-ligand or the assay-ligand, can be immobilized and the assay-ligand can be measured by a non-destructive technique, such as fluorescence. The device includes a detector which is constructed so that the field of view of the detector is primarily the region of either the immobilized substance or the region of the non-immobilized substance. The instrument responds to varying constant concentrations of the assay-ligand, since the assay-ligand will cause a change in the amount of the optically measured compound, usually the competing-ligand, within the field of view of the detector.

A primary advantage of this invention is that the response of the instrument is related to the chemical equilibrium properties of the combination receptor-site/competing-ligand/assay-ligand and therefore will not be affected by fouling of the membranes which separates the reaction system from the fluid to be assayed.

As an example, a glucose sensor is based on the competitive binding of glucose and a competing ligand substance, to a protein with suitable specific binding sites. An example of such a protein is the lectin, concanavalin (Con-A). The affinity of various sugars to Con-A has been intensively studied, and some of the values are given in Table I below. Of the low molecular weight sugars present in the blood, the concentration of which is shown in Table II, only glucose will show significant binding to Con-A.

TABLE I

| Binding Constants of Sugars to Concanavalin-A | |
|---|---|
| Sugar | K (mole/liter) |
| Isomaltose | $1.8 \times 10^{-4}$ |
| Maltose | $3.5 \times 10^{-4}$ |
| Fructose | $7.3 \times 10^{-4}$ |
| Glucose | $1.7 \times 10^{-3}$ |
| Sucrose | $1.9 \times 10^{-3}$ |
| p-nitrophenol-$\alpha$-D mannopyranoside | $2.94 \times 10^{-5}$ | from So and Goldstein, Biochem., Biophys. Acta 165, 398 (1968).

TABLE II

| from Geigy Scientific Tables 7th Ed. | |
|---|---|
| Carbohydrate | Concentration |
| Glucose | 800–1000 mg/l whole blood |
| Pentoses | 4 mg/l whole blood |
| L-Xylulose | 1 |
| Galactose | 16 |
| Mesoinositol | 6 |
| Glucose-6-Phosphate | 25 |
| Fructose-6-Phosphate | 5 |
| Fructose-1,6-Phosphate | 5 |

TABLE II-continued

| from Geigy Scientific Tables 7th Ed. | |
|---|---|
| Glucuronic Acid | 40 |

Polysaccharides and cells are known to bind to Con-A as well but are excluded from the glucose sensor chamber by a dialysis membrane barrier.

The principle of operation of the glucose sensor is based on the replacement of competing-ligand in the competing-ligand/Con-A complex by glucose with the concurrent release of the competing-ligand from such competing-ligand/Con-A complex. The following equilibria are involved:

Con-A + Glucose ⇌ Con-A/Glucose

Con-A + Competing ⇌ Con-A/Competing-Ligand
Ligand

Increasing the concentration of the glucose shifts the first reaction to the right and the second to the left.

If Con-A is immobilized outside the view of the detector, then the Con-A/Competing-Ligand complex is also outside the view of the detector. Thus the detector will respond primarily to the free competing-ligand concentration which increases with increasing glucose concentration. Alternatively, if there is an observable difference in some property of the competing-ligand when free and bound, or in the binding protein (e.g. Con-A) when free and bound with competing ligand, then the amount of glucose present can be inferred from the position of the second equilibrium.

For example, G. S. Hassing, and I. J. Goldstein, EUR. J. Biochem. 16, 549 (1970) have shown that the UV spectrum of p-nitrophenyl $\alpha$-D-mannoside is changed upon binding to Con-A. W. Bessler, J. A. Shafer and R. J. Goldstein, in the J. Biochem., 249, 2819 (1974), have used this property to determine the competitive binding affinity of other ligands by spectrophotometric methods. R. D. Poretz and I. J. Goldstein, in Biochem. Pharm., 20, 2727 (1971) have also shown that it was feasible to assay mannose and glucose by the inhibition of the Con-A/glycogen interaction by measuring turbidity changes. D. R. Dean and R. B. Homer, in Biochem, Biophys. Acta, 322, 141 (1973) have shown that fluorescense quenching occurs when 4-methylumbelliferyl $\alpha$-mannopyranoside binds to Con-A.

Figures 1, 1A, 4, 6:
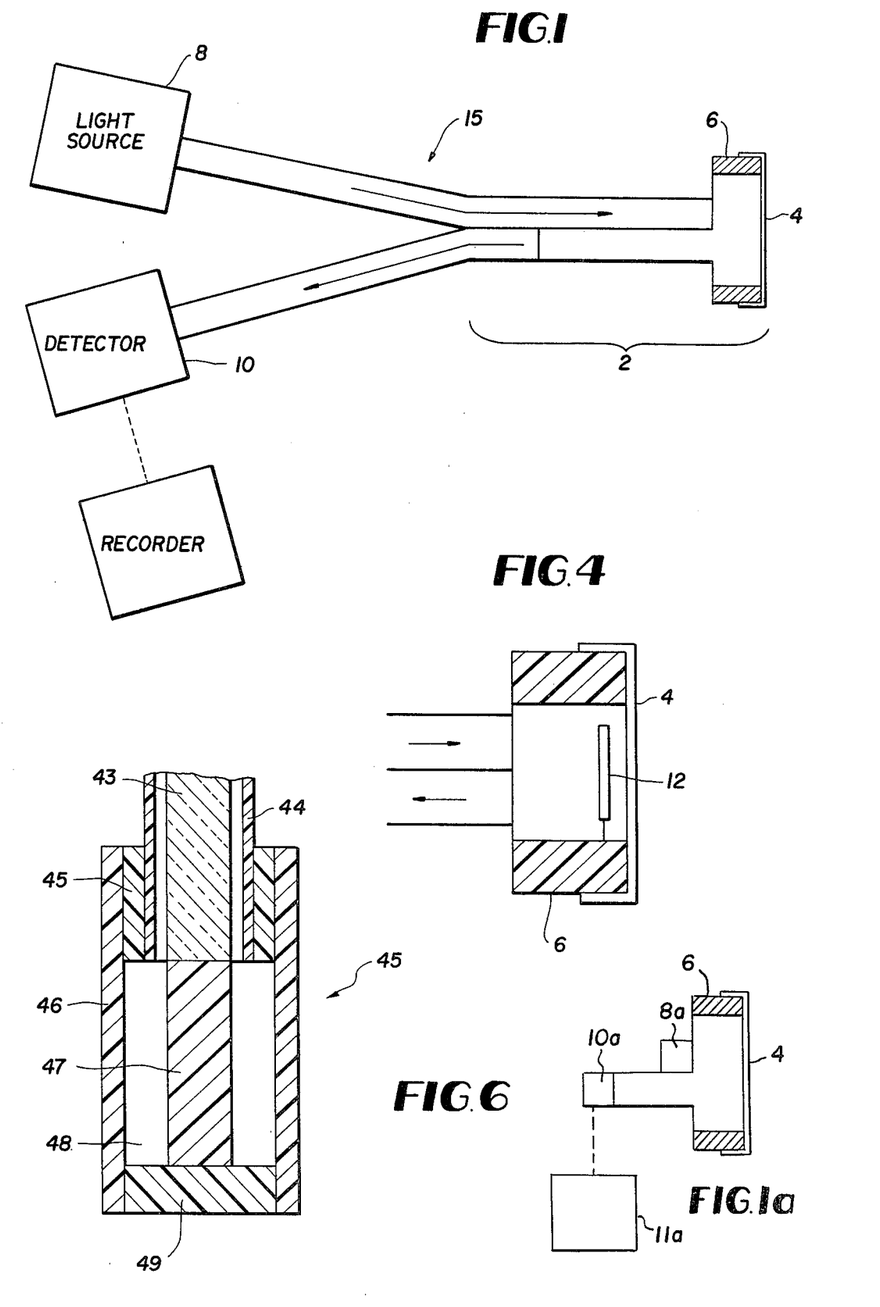
FIG. 1 is a schematic side view of a first embodiment of a device in accordance with the invention.
FIG. 1a is a schematic view of another embodiment of such a device.
FIG. 4 is a partial schematic side view, similar to FIG. 1, of a second embodiment of a device of the present invention.
FIGS. 6 and 8 are schematic side views of fourth and fifth embodiments, respectively.

A glucose sensor 15 is shown in FIG. 1, and comprises a chamber 2 which communicates with the blood through a dialysis (molecular sieve) membrane 4. Inside the chamber is immobilized Con-A, and a non-dialysible competing-ligand. A substance such as fluoroscein labelled dextran or other chromophoric material, incapable of passing through the membrane 4, can be used as the competing-ligand. In one embodiment, as shown in FIG. 1 the chamber includes a fiber-optic catheter connected to an external light source 8, and an external optical detector and displayer 10. In another embodiment, as shown in FIG. 1a, a miniaturized light emitting diode and photocell 8a are disposed in the chamber along with a radio transmitter to transmit the signal from the photocell 10a to a recorder and displayer 11a.

The free fluoroscein labelled dextran fluoresces when illuminated by light. The Con-A in the chamber is immobilized, for example, by using Con-A sepharose, a commercial preparation of Con-A immobilized to a gel. The light source 8 directs light at the solution containing the free labelled dextran. The immobilized Con-A sepharose 6 is placed outside the field of view of the incident light path. The dextran which has combined with the immobilized Con-A is therefore outside the path of the incident light. Dextran competes with glucose for binding sites with the immobilized Con-A. Therefore, all the dextran is not free in the solution to be illuminated by the incident light. The intensity of the light emitted from the dextran and detected by detector 10 is related to the amount of free and bound fluoroscein-dextran, which can be related to the glucose concentration in the sensor.

Figures 5A, 5B:
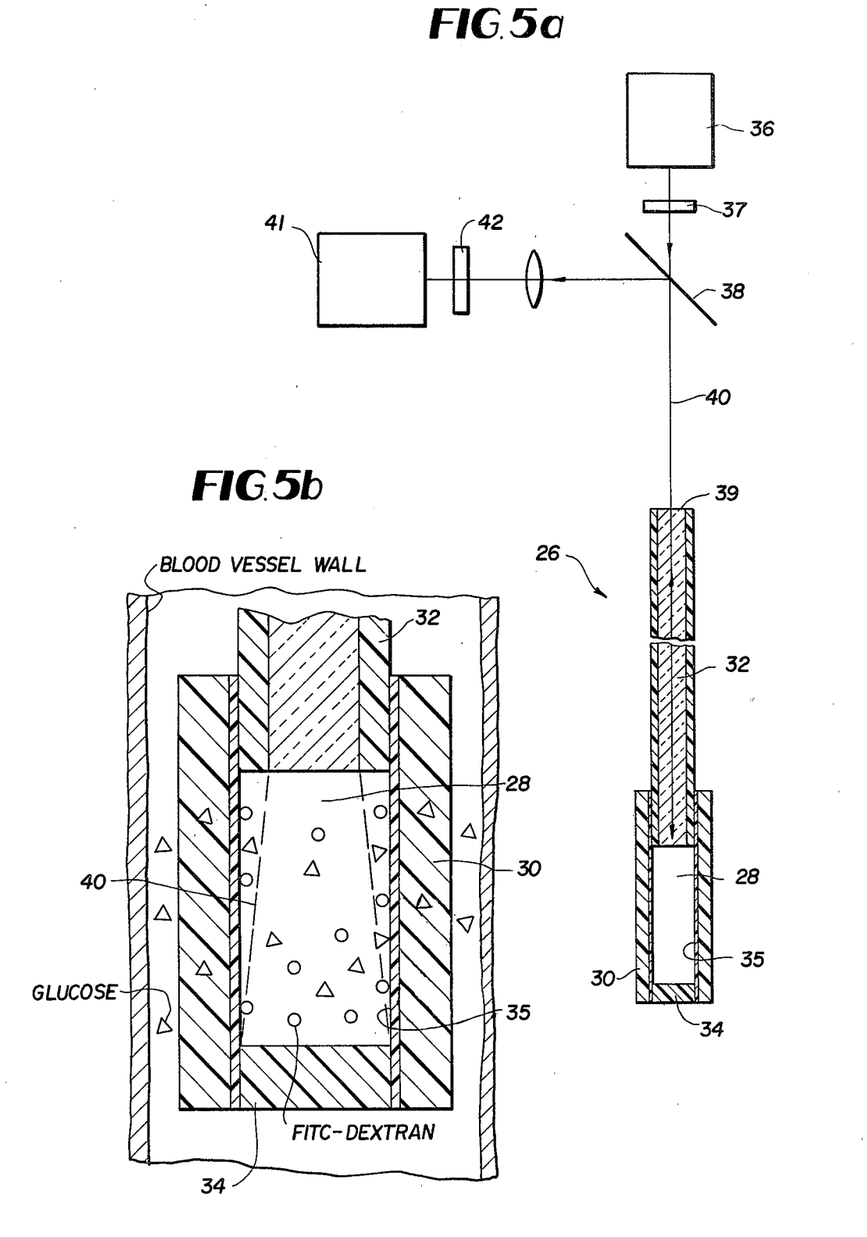

Referring to FIG. 5a, a sensor 26 comprises a chamber 28, created by a cylindrical hollow dialysis fiber 30, with a single optical fiber 32 inserted in one end and a plug 34 inserted in the other end. The interior surface of the hollow dialysis fiber 30 is coated with an immobilized but permeable layer 35 of Con-A. A solution in chamber 28 contains an appropriate amount of the competing-ligand, FITC-Dextran. The dialysis fiber 30 is inserted into a blood vessel where its exterior is bathed with blood. Glucose molecules in the blood communicate with the chamber 28 by diffusion through the walls of the hollow dialysis fiber 30. The porosity of the hollow fiber 30 and molecular size of FITC-Dextran are chosen such that the competing-ligand cannot diffuse out through the wall of the fiber 30 which serves as a dialysis membrane, and thus the FITC-Dextran is trapped within the chamber 28.

Excitation light 40 from source 36 passes through a filter 37, a half-silvered mirror 38 and focuses on the other end 39 of the optical fiber 32. The numerical aperture (NA) of the optical fiber 32 is chosen to be small as possible so that a minimum of the excitation beam 40 in the chamber intercepts the immobilized Con-A 35 in the chamber 28 of the hollow dialysis fiber 30; an NA of 0.15 is suitable. Unbound FITC-Dextran within this excitation beam 40 fluoresces and a part of this emitted fluorescense enters the optical fiber 32 and is transmitted through the other end 39. This emitted beam 40 is reflected into the light detector 41 through another filter 42. Filters 37 and 42 are chosen to minimize overlap in the spectrum of the excitation beam and emitted fluorescence.

In this configuration, some fluorescence of free FITC-Dextran is measured by the light detector 41 in the absence of glucose in the surrounding medium as predicted by the following chemical equilibrium:

FITC-Dextran(free) + Con-A(bound) ⇌ FITC-Dextran/Con-A(bound)

When glucose is present in the external medium, it will diffuse into the chamber and also bind to the immobilized Con-A according to the chemical equilibrium:

Glucose(free) + Con-A(bound) ⇌ Glucose/Con-A(bound)

Figure 3:
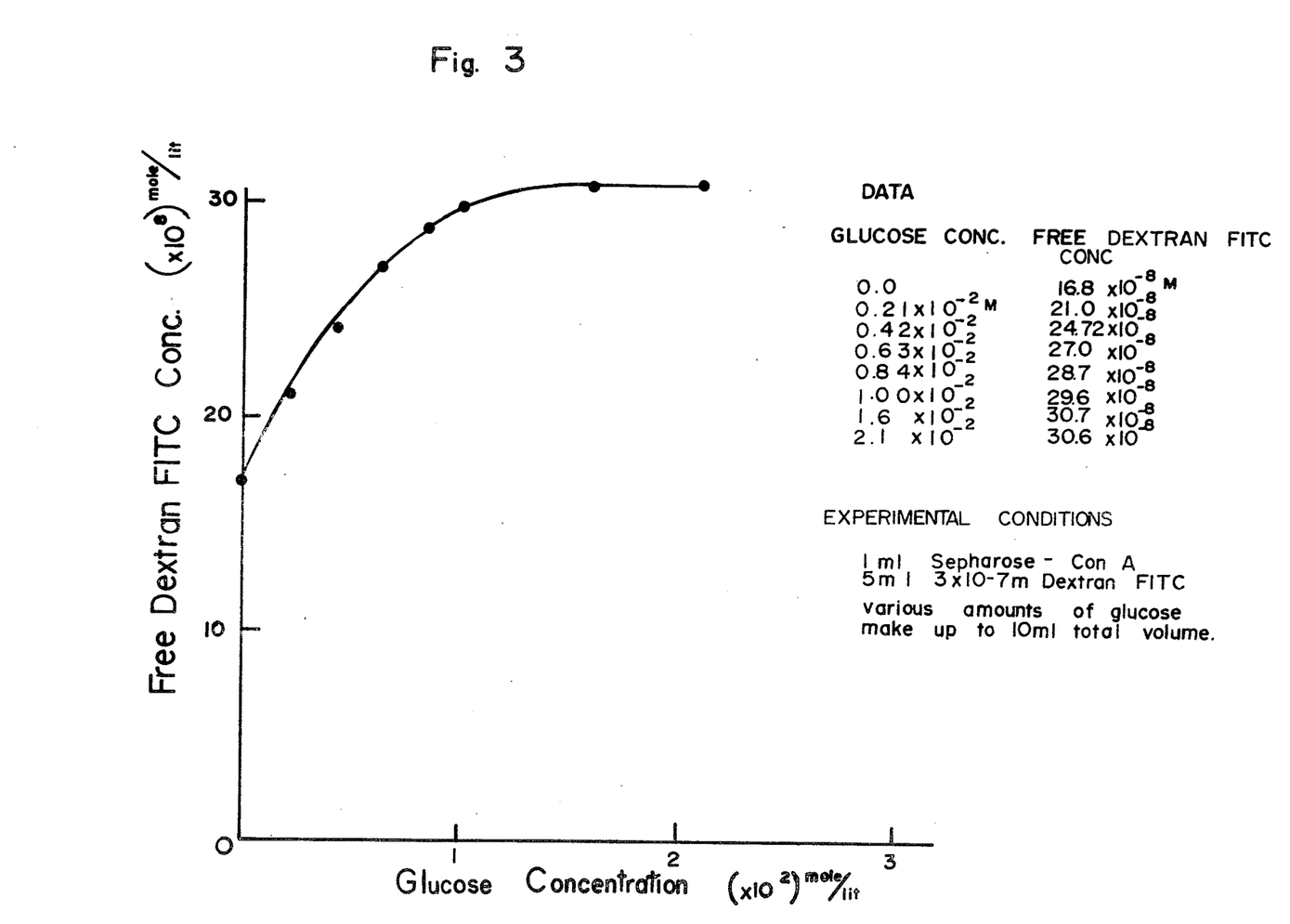
FIG. 3 is a graph showing the release of Dextran-FITC from immobilized Con-A with exposure to increasing amounts of glucose.

Due to the competition between glucose and FITC-Dextran for Con-A receptor sites, the concentration of free FIIC-Dextran will increase and an increase in the intensity of emitted fluorescence will be measured by the light detector 41. Thus increases in glucose concentration in blood will result in corresponding increases in the detector output. FIG. 3 shows the release of FITC-Dextran from immobilized Con-A with exposure to increasing amounts of glucose.

In one embodiment, the sensor assembly 26 is put into contact with blood by inserting it through a hypodermic needle which enters a vein. In this case, the optical components 36, 37, 38, 41 and 42 are outside the body. In another embodiment, these components can be miniaturized by using a light emitting diode LED for the light source 36 and a photodiode for the light detector 41, and the whole assembly implanted into the body.

Figure 7:
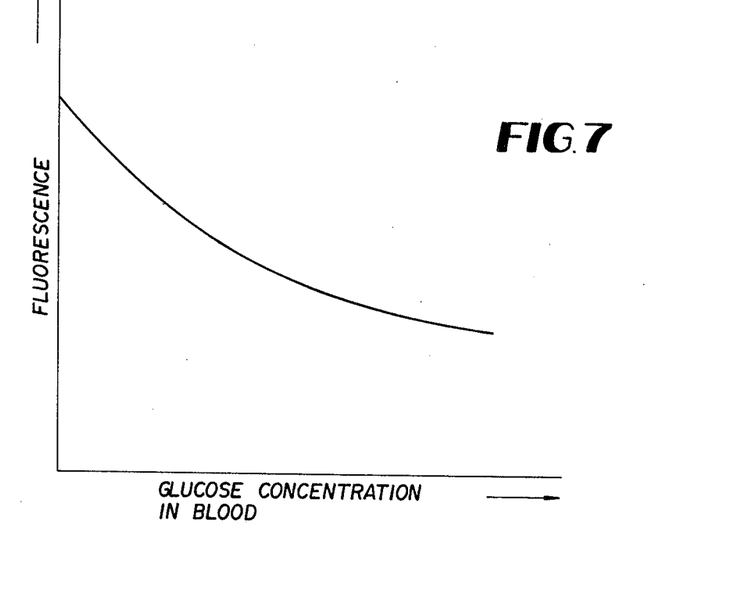
FIG. 7 is a qualitative graph illustrating the relationship between fluorescence and glucose concentration.

In another embodiment 45, FIG. 6, light from the light source is preferably directed to a gel 47 containing immobilized Con-A. The gel 47 may be retained in the light path by any suitable means such as a screen. In this case, the chamber 48 is formed by a hollow dialysis fiber 46 with the optical fiber 43, having cladding 44, inserted in one end. An additional spacer 45 is used to adjust the volume of the chamber 48 to the volume of the gel 47 containing immobilized Con-A. A plug 49 seals the bottom of the chamber. The response measured is due to the fluorescence of the FITC-Dextran in gel, some of which will be bound to the immobilized Con-A and some of which will be in the interstitial fluid within the gel. The effect of increasing glucose concentration of the response of the system is shown in FIG. 7.

In still other embodiments, dextran is labelled with a dye-like substance causing the dextran to absorb light in a certain wavelength range. Examples of systems working on the principle are given in FIGS. 4 and 8. Some of the light incident upon the free dye-labelled dextran or upon the dye labelled dextran/Con-A complex is absorbed and by the proper placement of optics in the chamber, the light unabsorbed by the dye labelled dextran is directed into the detector, thus giving a reading of the light absorbed by the dextran and thus of the glucose concentration. For example, noting FIG. 4, a mirror 12 is placed in the chamber to reflect to the detector all light from the light source which has not been absorbed by the light absorbing free competing ligand, e.g. the free dye-labelled dextran.

Figure 8:
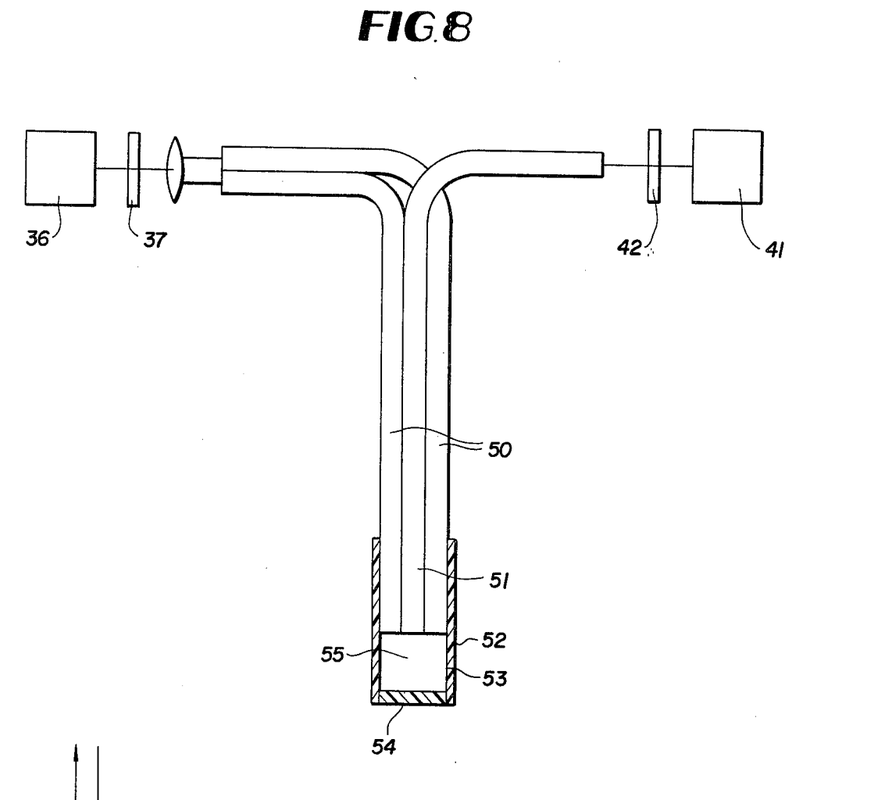

In the FIG. 8 embodiment, two or more optical fibers are used, a fiber 50 to bring light of the proper wavelength band into the chamber 55 and a fiber 51 to measure the light absorption of the solution in the chamber 55. At the bottom of the chamber formed by the hollow fiber 52 coated with Con-A 53, a plug with a mirror coating 54 is placed. Thus with increased glucose outside the chamber, increasing amounts of the light absorbing dextran will be displaced from the immobilized Con-A causing a decrease in light intensity measured by the detector system.

In another embodiment, using two or more optical fibers, light from the light source 36 can illuminate both the free FITC-Dextran and FITC-Dextran bound to the immobilized Con-A; however, the fibers are positioned so that fluorescence from either the free FITC-Dextran or bound FITC-Dextran is transmitted to the detector 41.

The required concentration of Con-A and the competing-ligand, for maximum sensitivity to glucose concentration, can be determined directly from the binding equilibria:

$$C + G \rightleftharpoons CG \quad K_G = \frac{C \cdot G}{CG}$$

$$C + D \rightleftharpoons CD \quad K_D = \frac{C \cdot D}{CD}$$

where C is the concentration of free Con-A sites, G is the concentration of free glucose, and D is the concentration of the competing ligand. Then one obtains $$\frac{G}{K_G} = \frac{D}{K_D}\left[\frac{\overline{C}/K_D}{\overline{D}/K_D - D/K_D} - 1\right] - 1$$

where $\overline{C}$ and $\overline{D}$ are total concentrations, i.e. free and bound forms.

Figure 2:
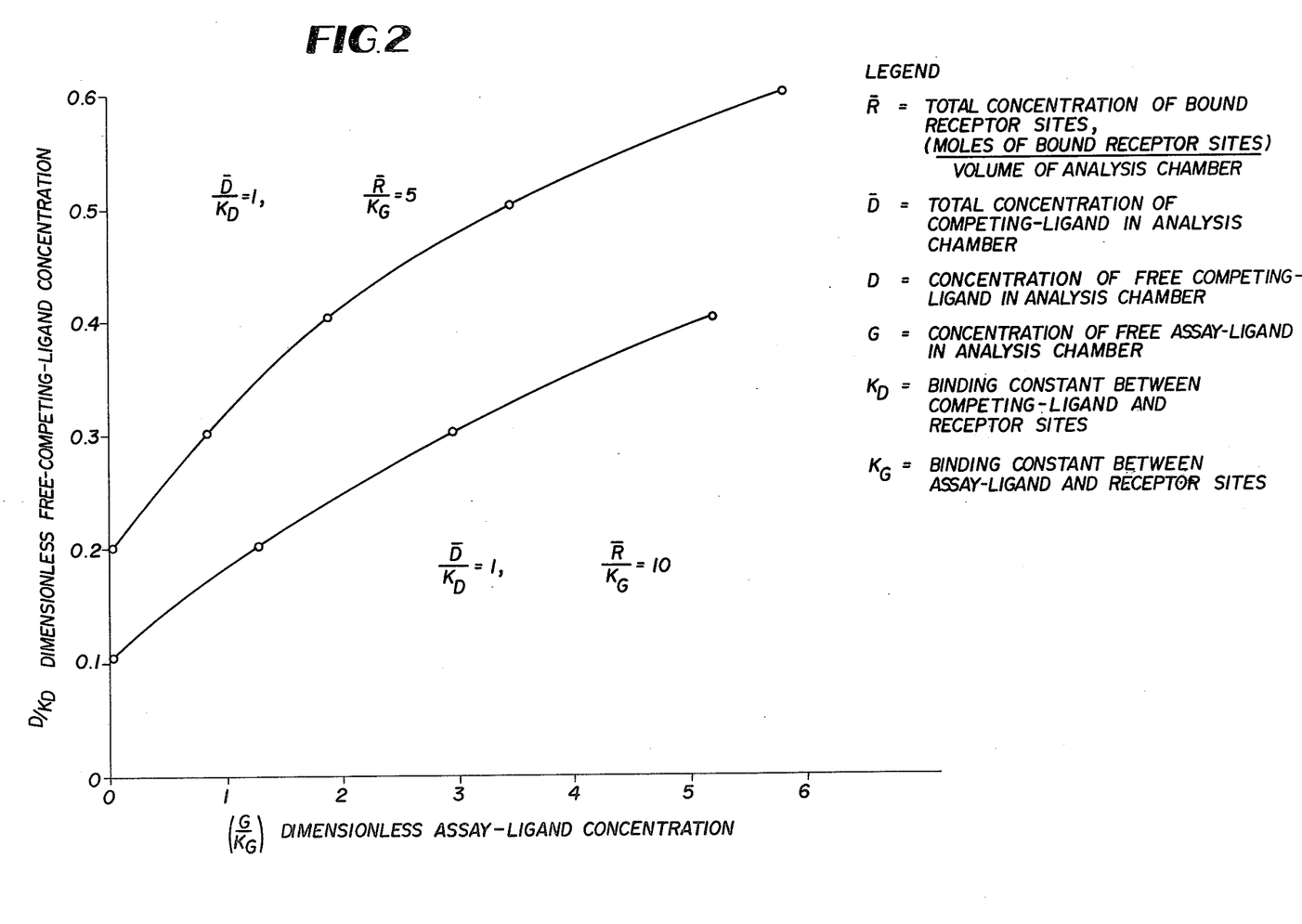
FIG. 2 is a graph showing curves relating the normalized concentration of the free competing-ligand to the normalized glucose (assay-ligand) concentration, calculated for a variety of assumed binding constants and immobilized receptor site concentrations.

Curves relating normalized D concentration ($D/K_D$) to the normalized glucose concentration ($G/K_D$) have been calculated for a variety of assumed binding constants $K_D$, and Con-A concentrations, and are shown in FIG. 2. It can be seen that there are a range of conditions where the measured response, i.e. free D concentration, is directly related to the glucose concentration in the sensor. As a point of reference, the glucose content of adult blood is about $5 \times 10^{-3}$M, so that on FIG. 2 the normalized glucose concentration ($G/K_G$) is about 3.

Several binding agents can be incorporated into the same sensor, each capable of binding a different low molecular weight plasma constituent, such as sugars, amino acids and hormones. In that case a set of corresponding competing ligands having different optical properties (i.e. fluorescing at different wavelengths) will also be provided in the sensor, one competing ligand for each plasma constituent to be measured.

The present invention has the following advantages:
electrical connections to the body are not required as they are with an electrochemical probe;
the device can be easily calibrated by determining the spectrum of the various compounds in the chamber when the chamber is exposed to known quantities of assay ligands;
the steady output of the chamber is not affected by fouling of the membrane and the device response will be stable for long periods of time;
the device can be used to measure any low molecular weight substance which can diffuse from body fluids across a dialysis membrane; and
the invention can measure not just the concentration of a class of compounds, such as sugars, but can measure the concentration of specific compounds within a class, such as glucose. This high specificity can be achieved because of the availability of many specific exchangers, such as enzymes and binding proteins.

The device can be used to measure low molecular weight compound in other complex fluids such as fermentation media, waste treatment streams, and food products.

It will be obvious to those skilled in the art that various changes may be made without departing from the scope of the invention and the invention is not to be considered limited to what is shown in the drawings and described in the specification.

What is claimed is:

1. A device to optically measure the concentration of low molecular weight assay ligand, such as a plasma constituent, comprising:
   a chamber insertable into a blood vessel including a selection means, in a wall of said chamber, for allowing at least one low molecular weight assay ligand to enter said chamber;
   at least one competing ligand, inside said chamber, each said at least one competing ligand having a different identifiable optical property from the assay ligand to be measured, a quantitative measurement of said optical property being proportional to the concentration of said competing ligand, each said at least one competing ligand being a material which will not pass through said selection means;
   at least one binding means having binding sites, confined inside said chamber in a selected region, for reversibly binding with the low molecular weight assay ligand to form a first complex of the binding means and assay ligand, and for reversibly binding with said competing ligand to form a second complex of the binding means and competing ligand, said competing ligand competing with the assay ligand for binding sites on said binding means;
   a light source means in optical contact with the interior of said chamber for illuminating the unbound competing ligand and/or the second complex within said chamber; and
   a detecting means in optical contact with said chamber for quantitatively measuring the indentifiable optical property of substantially only the unbound competing ligand or of substantially only the second complex.

2. A device according to claim 1, wherein said chamber is a part of a catheter.

3. A device according to claim 1, wherein said chamber is a part of a fiber optic catheter, said detecting means and said light source means being in said optical contact with said chamber through optic fibers.

4. A device according to claim 1, wherein said selection means is a dialysis membrane.

5. A device according to claim 4 wherein the identifiable optical property of each said at least one competing ligand is the absorption of light of particular wavelengths, and further including
   a mirror, disposed inside said chamber so as to reflect the light passing through said unbound competing ligand or said second complex into said detecting means.

6. A device according to claim 1, wherein said competing ligand is chromophoric material.

7. A device according to claim 1, wherein said competing ligand is fluorecing labelled dextran, said binding means is concanavalin-A, and said assay ligand is glucose.

8. A device according to claim 1 or 7, wherein said light source is external to said chamber and communicates with said chamber by optic fibers.

9. A device according to claim 8, wherein said detecting means is external to said chamber and communicates with said chamber by optic fibers.

10. A device according to claim 1, wherein said light source is a light emitting diode in said chamber, and said detecting means includes a photocell in said chamber.

11. A device according to claim 10, further including recording means for recording the measurements made by said detecting means, and communication means for permitting communication between said recording means and said detecting means by radio waves.

12. A device according to claim 1 further including recording means for recording the measurements made by said detecting means.

13. A device according to claim 1, further including a plurality of binding means, inside said chamber, each binding means reversibly binding with a different assay ligand; and a plurality of competing ligands, inside said chamber, there being one competing ligand for each binding means to compete with the assay ligands for binding with said corresponding binding means.

14. A device according to claim 1, wherein the selected region for confining said binding means is located outside the light path.

* * * * *

UNITED STATES PATENT AND TRADEMARK OFFICE
CERTIFICATE OF CORRECTION

PATENT NO. : 4,344,438
DATED : August 17, 1982
INVENTOR(S) : Jerome S. SCHULTZ

It is certified that error appears in the above-identified patent and that said Letters Patent are hereby corrected as shown below:

Column 4, line 61, after "diode" insert --8a--; after "photocell" delete "8a" and insert --10a--

Claim 7, line 2, "fluorecing" should read --fluorescing--

Signed and Sealed this

Third Day of May 1983

[SEAL]

Attest:

GERALD J. MOSSINGHOFF

Attesting Officer  Commissioner of Patents and Trademarks